United States Patent [19]

Barringer et al.

[11] Patent Number: 4,861,646

[45] Date of Patent: Aug. 29, 1989

[54] CO-FIRED METAL-CERAMIC PACKAGE

[75] Inventors: Eric A. Barringer, Waltham; Sheldon I. Lieberman, Burlington; Mark S. Schmidt, West Newton; James D. Hodge, Medway; Richard Waack, Wayland, all of Mass.; Donald J. Kelley, Suffolk, Va.; Brian W. Saxton, Norwell; William C. Gruber, Arlington, both of Mass.

[73] Assignee: Ceramics Process Systems Corp., Milford, Mass.

[21] Appl. No.: 85,950

[22] Filed: Aug. 13, 1987

[51] Int. Cl.$^4$ ................................................. B32B 18/00
[52] U.S. Cl. ....................................... 428/210; 156/89; 428/241; 428/325; 428/426; 501/2; 501/4; 501/5; 501/10; 501/11
[58] Field of Search ................. 156/89; 501/2, 4, 5, 501/10, 11; 428/195, 210, 241, 325, 426

[56] References Cited

U.S. PATENT DOCUMENTS 4,621,066 11/1986 Nishigaki ................................. 501/2
4,642,148 2/1987 Kurihara et al. ....................... 156/89

Primary Examiner—Caleb Weston
Attorney, Agent, or Firm—Bradley N. Ruben

[57] ABSTRACT

Glass-ceramic packages for integrated circuits containing multi-layer, interconnected thick film wiring patterns are obtained by co-sintering a glass-ceramic composite and copper, silver, palladium, gold, based conductors at temperatures not exceeding about 1000° C. The dielectric systems include composites of borosilicate glasses and crystalline fillers which are fabricated by either mixing glass frit and the filler or by a sol-gel coating process. The package is fabricated using a tape specifically designed for clean binder burnout in a reducing atmosphere at low temperatures and also for superior mechanical and thermal properties. Metallization, applied by the thick film screening technique, utilized herein has glass-ceramic bonding agents designed to promote adhesion yet maintain the desired electrical properties and post-processing characteristics.

20 Claims, No Drawings

CO-FIRED METAL-CERAMIC PACKAGE

BACKGROUND

1. Field of Invention

This invention relates to glass-ceramic composite packages for integrated circuits in general, and in particular to those containing multi-layer, interconnected thick-film wiring patterns obtained by co-firing a glass-ceramic composite and copper, silver, or gold based conductors at temperatures not exceeding about 1000° C.

2. Description of Prior Art

Multi-layer ceramic substrates for mounting integrated circuit chips generally comprise alternating layers of metallic circuits and ceramic insulating layers to form three dimensional interconnect circuits. The substrates are produced either by a thick film printing method or a green sheet lamination method.

The thick film printing method has been used to fabricate hybrid circuits and multi-layer printed interconnect boards. In this process, metal powders and ceramic powders are formulated into metal and dielectric (insulator) inks and then alternately screen printed onto a fired ceramic base. Generally two or three printings of dielectric material are required for every insulating layer and the circuit must be fired after each printing process. Thus, this method is very time consuming because of the large number of printing and firing steps required. The method is also prone to low production yields and is limited in the density of interconnect circuitry. Ceramic layer hermeticity is a major problem affecting yields and is a direct result of using screen printing methods to form insulating layers. In addition, conventional metal pastes contain active bonding agents to promote adhesion to ceramic substrates (e.g., lead borosilicate glass and bismuth oxide) which function acceptably in air fired applications, but which are problematic in nitrogen firing applications.

According to the green sheet lamination method, green ceramic sheets on which metal circuits have been printed are successively laminated and then co-fired to form a monolithic interconnect structure (package). Generally, the ceramic green tape is fabricated by the doctor blade casting process from a slurry containing a mixture of ceramic powders, thermoplastic resin, solvents, and other additives (dispersants, plasticizer). Polyvinyl butyral (PVB) is the most commonly used resin system for tape formation. The green tape is blanked into sheets and registration holes are punched. Via holes, which in the final package serve as vertical interconnects between layers, are punched using fixed tooling or a numerically controlled punch press. The via holes are filled and circuit trace patterns are printed using the desired metallization compositions. The individual sheets are then stacked in the proper sequence and laminated to form a solid, composite laminate. The laminate is fired to decompose and remove the organic binder and to sinter the ceramic and metal particles, thus forming a dense body containing the desired three-dimensional wiring pattern.

Aluminum oxide, because of its excellent electrical (insulating), thermal, and mechanical (especially strength) properties has been the ceramic of choice for such substrates. These ceramic bodies, generally containing 4-10 weight percent glass, require sintering temperatures above 1500° C., which thus necessitates the use of refractory metals such as molybdenum or tungsten for the wiring. These metals have poor electrical conductivity as compared to highly conductive metals such as copper, and secondly, they require the use of strongly reducing atmospheres during co-firing necessitating expensive furnace systems. Alumina has been an adequate dielectric material for microelectronic packaging in the past; however, the advent of higher frequency and higher speed devices has made clear the deficiencies of the current materials systems. $Al_2O_3$ has a relatively high dielectric constant of about 9.9, causing high signal propagation delay and low signal-to-noise ratio (crosstalk). Furthermore, alumina has a thermal expansion of $6.7 \times 10^{-6}$/°C. (20°-200° C. range) as compared to about $3.0-3.5 \times 10^{-6}$/°C. for silicon, which represents significant mismatch in thermal expansion and results in design constraints and reliability concerns (e.g., flip chip technology). Furthermore, the binders used to fabricate green tape do not decompose cleanly during firing at low temperatures (200°-600° C.) in the reducing atmospheres utilized; significant graphitic carbon is generated which requires a high temperature burnout treatment (1100°-1200° C.) prior to raising the temperature to the peak firing condition.

Accordingly, there exists a need for a materials system which allows co-sintering of the ceramic with a conductive metal such as copper, gold, or silver. An IC package fabricated from this system would have significantly improved signal transmission characteristics. To this end, a glass-ceramic material sinterable to a high density at temperatures less than 1000° C. is desirable. To allow co-sintering with copper in a reducing atmosphere, in particular, the binder material must depolymerize and burnout cleanly, which precludes the use of conventional binders such as PVB. PVB or similar polymers would result in a porous ceramic and carbonaceous residue, thereby deteriorating the mechanical strength and electrical insulation. There also exists a need for a metallurgical system that yields good conductivity, adhesion and solderability when co-fired with the ceramic dielectrics. Furthermore, for optimum yields and performance, the bonding agents and ink vehicle system should be compatible with gold, silver/palladium alloys, and copper and should be free from bismuth- and/or lead-containing compounds.

There have been numerous attempts to make such a low temperature co-firable substrate; see for example: Utsume, et al., U.S. Pat. Nos. 4,536,435; Takabatake, et al., 4,593,006; Herron, et al., 4,234,367; Kamehara, et al., 4,504,339; Eustice, et al. (IEEE 36th ECC Proceedings, 1986, pp. 37-47); Nishigaki, et al., Proceedings of the 1985 International Symposium on Microelectronis (ISHM), pp. 225-234. Although some similarities exist between this art and the present invention, critical differences and improvements are realized in the present invention. With the exception of Herron, et al., who utilize a cordierite glass-ceramic, the above generally use $Al_2O_3$ glass composites fabricated by mixing $Al_2O_3$ powder and glass frit. These composites generally have dielectric constants between 7.0 and 8.0, higher than what would be desirable in an advanced electronic package.

A second area of importance to the co-fired package, for which the present invention provides improvements, is metallization composition and firing atmosphere. Noble metals, such as gold, silver, and silver/palladium alloys, have received primary focus in the prior art because these metals can be co-fired in an air atmosphere and the tape system can utilize state of the art binder technology. Herron, et al. and Kamehara, et al. focus on copper metallurgy and firing in a nitrogen atmosphere containing water vapor to aid in binder removal. Herron, et al. disclose a cordierite glass-ceramic with copper metallization; however, in this case the very low thermal expansion coefficient of cordierite ($1-2 \times 10^{-6}/°C$) as compared to copper ($17 \times 10^{-6}/°C$ coupled with the low strength of their cordierite make fabrication yield and reliability problematic. Fracture in the glass-ceramic around metallization, especially vias and attached leads or pins, caused by the differential thermal expansion induced stresses during thermal cycling is particularly problematic. In addition, proper crystallization of the cordierite glass-ceramic during binder burnout and co-firing can be difficult to control. Kamehara, et al. disclose a low strength (28,000 psi), yet higher thermal expansion of their glass-ceramic ($4.5 \times 10^{-6}/°C$), thus thermal expansion mismatch may not be as serious.

Kamehara et al. further disclose the addition of as much as 1% alkali oxide to the glass ceramic, which provides alkali ions that are known to enhance copper (or silver if applicable) migration in the glass during co-firing, which may lead to degradation of electrical insulating properties. Furthermore, the type of copper ink disclosed (Du Pont 9923) is known to contain bismuth oxide and/or a lead borosilicate glass, which are subject to reduction to metallic bismuth and lead during firing in the reducing atmospheres required for copper co-firing, an effect which may lead to degradation of the conductor properties. They also disclose a method of providing vias which entails filling the vias with a row of copper balls; the advantages and usefulness of this method is not made clear. However, this method seems less practical than the presently accepted screen printing method for vias using metal inks.

DISCLOSURE OF THE INVENTION

We have succeeded in making glass-ceramic composites suitable for use as ceramic substrates which have a sintering temperature of approximately 1000° C. or less. Thus, these composites may be co-sintered with copper or other highly conductive metals having relatively low melting points. These composites comprise a variety of crystalline ceramic fillers and a borosilicate glass and are fabricated by either mixing the filler powders with a glass frit or by a sol-gel coating process of the filler. By varying the composition of the composite, one can select sets of properties, primarily fracture strength, dielectric constant, and thermal expansion coefficient, for the desired application.

The present invention employs $Al_2O_3$ and additional ceramic fillers, such as cordierite and quartz, to yield low dielectric constants. These composites are fabricated using either the mixed powder method (ceramic filler plus glass frit) or a sol-gel coated filler method, where the glass coated filler powder is processed as a single powder type rather than mixing two separate powders. This provides additional control of the tape fabrication process and a more homogeneous product. Additionally, glass compositions not possible as single phase glasses from the melt can be utilized through the sol-gel coating approach. Another important feature of the glass-ceramic dielectric is fracture strength; to allow reliable coexistence of the ceramic and the metallurgy a high strength (approximately $\geq 30,000$ psi) is desirable. The glass-ceramics materials from the cited references generally exhibit fracture strengths below about 30,000 psi, whereas the present invention provides composites having strengths up to about 45,000 psi.

We have also succeeded in designing a binder system which yields high quality green tapes and burns out cleanly in air and in reducing atmospheres required for co-sintering the composites with copper. These tapes have excellent thermomechanical properties, such as tensile strength, modulus, creep resistance, and dimensional stability, thus allowing precision fabrication of circuit patterns.

Finally, we have succeeded in the formulation of metal inks for both circuit traces and vias which utilize glass-ceramic bonding agents to provide for acceptable bond strength, shrinkage match, thermal expansion match, solderability, and other properties. These compositions are also co-fired without blistering and with minimal migration (copper and silver). These materials in combination provide numerous benefits to the manufacturer, both in terms of enhanced products and lower production costs.

DESCRIPTION OF THE SPECIFIC EMBODIMENTS

The low firing temperature materials of the present invention are glass-ceramic composites comprising a borosilicate glass and a ceramic filler. The glassy material mixed with or used to coat the filler particles is generally a composition based on calcium oxide (CaO), magnesium oxide (MgO), boron oxide ($B_2O_3$), and silicon dioxide ($SiO_2$) or combinations of these materials. Aluminum oxide ($Al_2O_3$) and other oxide additions to the glass can be made to alter the properties of the glass and the subsequent composites.

The preferred glass compositions include those described in detail in co-pending U.S. patent application Ser. No., 07/085,078, (now U.S. Pat. No. 4,788,046 filed contemporaneously herewith, which is hereby incorporated herein by reference. They are in the range of approximately 20-57% alkaline earth oxides (MO), 23-40% $SiO_2$, 20-35% $B_2O_3$, and 0-10% $Al_2O_3$. The preferred compositions for fritted glass (powder) prepared from essentially single phase glass melts are 25-57% MO, 23-35% $SiO_2$, 25-35% $B_2O_3$, and 0-10% $Al_2O_3$, where in both cases the preferred percentage of alkaline earth oxide present as MgO is 0-50% and the balance thereof is CaO. For fritted glass materials, reducing the MO or $B_2O_3$ levels below the above values or increasing the MgO ratio much above 50% leads to two-phase, and sometimes devitrified, glasses which may also be difficult to batch and melt. Glasses which have phase separated, but not devitrified, have been successfully employed, yet they are not generally preferred.

The filler material of the composite is generally a crystalline ceramic, including alumina, spinel, or almost any silicate-based oxide material, including cordierite, mullite, forsterite and quartz, or any combination of the foregoing. The filler material and the appropriate glass can be chosen to optimize a desired characteristic. For example, in one embodiment an alumina filler might be chosen because of the strength imparted to the fired product. In a further embodiment, alpha-cordierite yields composites with a lower thermal expansion coefficients, which more closely matches that for silicon, and lower dielectric constants (about 5.5). In yet another preferred embodiment, crystalline quartz yields composites with a higher thermal expansion coefficient and a very low dielectric constant of 4.5 to 5.5, depending on the glass used. Additionally, although not a crystalline ceramic filler, fused $SiO_2$ has been successfully employed; during firing the $SiO_2$ reacts with the glass to form a crystalline (primarily cristobalite) $SiO_2$-glass composite.

In a preferred embodiment where reproducibility is important, the particles have a narrow size distribution. As used herein, the term "narrow size distribution" refers to particles whose size range has a standard deviation not greater than approximately 50% of the mean. However, the invention is equally applicable to particles with conventional size distributions. The particles of the present invention preferably have an average diameter of 0.5-5 micrometers, and generally those with a diameter of 3 micrometers or less are more preferred. However, it is to be understood that for this invention the size of the particles is not critical, and the invention is applicable to particles of other diameters outside the foregoing range.

The preferred range of constituent ratios for the starting powders are 40-75% filler using the sol-gel coating method and 40-60% filler for the mixed powder method. The upper limit in filler content was established by sinterability requirements for temperatures less than approximately 1000° C. The upper limit of 60% filler for the mixed powder method is similar to previously disclosed values, yet similar densities are achieved with as much as 15% more filler using sol-gel coated fillers. The lower limit of 35-40% filler was established because of significant degradation in firing behavior and of key properties below this level, especially for the alumina-based glass-ceramics. Fracture strengths as high as 45,000 psi were achieved for 60% filler, whereas the strength rapidly decreased toward that for bulk glass (about 20,000 psi) as the $Al_2O_3$ level was decreased below 40% ($Al_2O_3$ only filler present). In addition, sticking of the composite to the setter during firing becomes a significant problem at high glass content.

The high fracture strength observed herein, especially for the alumina-based composites, is due to two factors. The most important factor, which is specific to the $Al_2O_3$ filler, is the dissolution of a small amount of $Al_2O_3$ into the glass during firing ($T \geq 800°$ C.), which reacts with the glass to form anorthite ($CaO-Al_2O_3-2SiO_2$). An added benefit of this reaction is that the fired $Al_2O_3$-based composites may be heated in further processing (brazing) to temperatures near the peak firing temperature without causing warpage of the body. A second factor influencing fracture strengths, and in fact leading to more uniform properties in general, is the more uniform fired microstructures resulting from homogeneous, well dispersed slips used in green tape fabrication; this point is discussed further in a subsequent paragraph.

It is preferred that the filler not react excessively with the glass, because this results in uncontrolled shrinkage and excessive warpage during firing and also generally leads to degraded properites, particularly fracture strength. To moderate any effects of reactions, the filler or glass may be altered. In one preferred embodiment, a mixture of fillers, one reactive and the second relatively inert, may be combined to yield more desired net properties than the two separately. For example, $Al_2O_3$ at 60% mixed with glass containing 30.5% $SiO_2$, 31.5% $B_2O_3$, and 38.0% CaO yields high fracture strengths and dielectric constants of about 7.9, while forsterite (50%) mixed with the same glass reacts without densification during firing up to 1000° C. However, a combination of the three constituents, for example, densifies acceptably and yields high fracture strength and reduced dielectric constant.

A preferred embodiment of the present invention is the combination of cordierite, $Al_2O_3$ and a calcium magnesium borosilicate (CMBS) glass to yield good net properties, particularly fracture strength (30,000-40,000 psi), dielectric constant (about 5.5-6.5) and thermal expansion coefficient (approximately $4 \times 10^{-6}/°C$.) Another preferred embodiment of the present invention is the combination of quartz and glass with $Al_2O_3$ and/or cordierite to yield comparable properties.

Another preferred embodiment of the invention is the use of MgO additions to the glass phase of the final composite, either in the form of a reactive filler, such as forsterite or cordierite added to a calcium borosilicate (CBS) glass, or as a CMBS glass, to impart chemical stability to the fired composites. Although Takabatake, et al. disclose the addition of $Al_2O_3$ to their glass to impart chemical stability, $Al_2O_3$ was not successful in the present case. During firing of Composite 1, $Al_2O_3$ and a CBS glass, some $Al_2O_3$ dissolves into the glass, but is subsequently consumed in forming anorthite, thereby leaving a residual borosilicate glass phase that is soluble in water. Hence the composite fails a water leaching test (2 hours in boiling water) for which $\leq 1\%$ weight loss is required. However, the addition of MgO to the composites significantly improves chemical stability; when anorthite forms during firing the MgO remains in the residual glass phase, thereby imparting stability.

Tape System

The multi-layer interconnect packages are fabricated using sheets of green ceramic tape, which are punched, printed with metal inks, laminated together, and then fired. High yield fabrication of quality packages requires exacting properties from the green tape. Consistent and uniform particle packing density in the tape is required for control of green-to-fired shrinkage, among other properties. This consistency is strongly influenced by optimum dispersion of the powder particles in the casting slurry, discussed below, and control of the particle size distributions for the starting powders. Although wide particle size distributions, typical of commercially available powders, and a large range of average particle size for the fillers and glass, or sol-gel coated filler, can be successfully used for cofirable green tape, particle size control is preferred. In one embodiment, the average particle size for the fillers and glass frit or for the sol-gel coated filler should be between approximately 0.5 and 5 microns. In a further embodiment, the coarse portion of the particle distribution for each powder may be extracted by a classification process to set the upper particle size at the desired level. One such classification process is described in U.S. patent application Ser. No. 028,891, filed March 23, 1987, which is hereby incorporated herein by reference. In yet a further embodiment, the particle size distributions may be further narrowed by removing the fine portion at a desired size. The resultant controlled size distributions of fillers and glass for the mixed powder method or of coated filler from the sol-gel method yield tapes with superior reproducibility. Fired microstructures are also improved using these powders, although acceptable microstructures and properties for microelectronic substrates are possible using wide size distribution powders.

Green tapes are fabricated from slurries which contain at least one powder, a dispersant, solvents, a polymer, and a plasticizer. Specific binder systems which are detailed in co-pending U.S. application Ser. No. 07/085,951 filed contemporaneously herewith, which is hereby incorporated herein by reference are particularly preferred. Although conventional binder systems can be used, a purpose of the present invention is to provide a tape system that is cofirable with copper in a non-oxidizing atmosphere as well as with other metals in air. Hence, in such an atmosphere the binder must degrade readily and burn out cleanly; methacrylate polymers have been found to comply with this requirement. Compatible plasticizers for these polymers, such as phthalates and adipates, impart flexibility to the green tape. Solvents for these polymers and plasticizers are alcohols, ketones, acetates and aromatics, such as toluene and xylene. The dispersants used must be compatible with the solvent system, yet strongly adsorb onto the powder surface to impart colloidal stability to the particulate slurry.

The tape systems disclosed herein and in above-referenced application No. 07/085,951 have been found by us to also be suitable for transfer tape applications of the type disclosed in Vitriol, et al., Proceedings of ISHM, 1986, pp. 487–495. The key aspects of the tape are the ability to be fully laminated to a dense substrate, such as 96% $Al_2O_3$, without deformation of any pre-punched vias or cavities. During firing the dielectric material must fully adhere to the substrate and shrink in one direction to form a dense layer without closing down via holes. It is critical that the dielectric material have a thermal expansion coefficient closely matching that of the substrate to avoid excessive camber upon firing and cooling. The $Al_2O_3$- and quartz-based composites satisfy these requirements for $Al_2O_3$ substrates, while the cordierite-based composites are ideal for high thermal conductive substrates, such as refractory metals (molybdenum, tungsten), SiC and AlN which have a low thermal expansion coefficient. The latter class of substrates require firing in a neutral or reducing atmosphere ($N_2$ or $N_2/H_2$) making a tape having clean binder burnout is especially preferable. The tape system described herein is well suited for this application.

The ability to select thermal expansion coefficient for the composite also allows for the use of metallic plates brazed onto the bottom of fired packages. Metals such as Mo, W, and W-Cu alloys have thermal expansion coefficients between $4.5-6 \times 10^{-6}$, which are in the range provided by the present invention for the dielectric materials. Because of this match, plates of refractory metal or ceramic such as AlN and SiC may be brazed onto the bottom of fired laminates to provide packages having very high thermal dissipation characteristics. Thus a preferred embodiment of the present invention involves the combination in a package of a low temperature cofirable substrate with a high thermal conductivity plate.

Metallization

The conductor inks employed in the present invention generally contain a metal powder, powdered bonding agents, dispersant, solvent, and binder. Other additives may be present to adjust rheology of ink or properties of the fired metallization.

In a preferred embodiment of this invention, the metal is copper in the form of a relatively uniform and non-agglomerated powder whose average size ranges approximately 1-10 micrometers. It is preferred that the powder have a relatively narrow size range, but the invention is not limited to narrow size range powders, and is equally applicable to those having conventional sizes. A further embodiment, however, uses a blend of discrete sized particle populations to control the shrinkage during firing.

The ceramic-metal bond promoting agents of the present invention generally comprise a calcium magnesium borosilicate (CMBS) glass plus either cordierite, forsterite, alumina, quartz or a combination of these. We have found that it is desirable to use some of the same constituents in both the trace and via inks as are found in the substrate, albeit in differing amounts and proportions. This provides for more uniform shrinkage of the entire piece during firing, and an increased ability to withstand thermal stress. Further, it has been found that as one increases the percentage of cordierite, the thermal expansion coefficient decreases.

Metals which may be used in the ink formulations may be selected for desired characteristics, such as conductivity and melting point. Preferred metals for this invention include but are not limited to: copper, silver, palladium, gold, alloys including any of the foregoing, or mixtures of the foregoing.

The preferred composition for the solids portion of the inks of the present invention are as follows. For trace inks approximately 80-97 volume percent metal is preferred, with the balance being 3-20 volume percent additives for bond promotion or other desired properties, while in via inks the metal should make up approximately 40-70 volume percent, with the balance being 30-60 volume percent additives. Specific ink formulations are detailed in co-pending U.S. application Ser. No. 07/085,077, filed contemporaneously herewith, which is hereby incorporated herein by reference. Inks made in accordance with the present invention showed good printing characteristics and, upon sintering, adhered well to the ceramics. Typical resistivities for trace inks were approximately 1-2 milliohm/square, and for via inks were approximately 3-8 milliohm/square.

Firing

The temperatures for firing the packages of the present invention are typically less than 1000° C., and generally range from approximately 850°-975° C. For quartz-based substrates, the range is from approximately 875°-975° C.; for cordierite-based and alumina-based substrates from 875° to 950° is preferred. With alumina based substrates, temperatures of over about 1000° result in excessive reactions. It was found that the alumina and glass produce anorthite and the result is a substrate which does not become dense and is not heremetic. On the other hand, at temperatures much less than about 900°, the substrate has a glassy appearance rather than a crystalline one and migration of the metal may become a problem. At temperatures greater than about 900°, the substrate has the desired crystallized structure with little or no metal ion migration. After firing the substrate may contain a number of phases, including but not limited to: cordierite, spinel, glass, alumina, quartz, anorthite, other silicates and other materials.

A preferred firing schedule for copper co-firing controls time, temperature, and the atmosphere, and has two regions, a low temperature region (<800°) for binder burnout and a higher temperature region (>800°) for sintering. This is detailed as follows. From room temperature to approximately 700°-775°, the heating rate was 2°-3°/minute. (Alternatively, the temperature may be raised from room temperature to approximately 350° C. at 2°-3°/minute and then to approximately 700°-775° C. at 4°-6°/minute.) At 700°-775°, the temperature was maintained for 1-3 hours to ensure complete binder burnout. All the foregoing steps were conducted in a nitrogen atmosphere with 1-20 ppm $O_2$ and 2-5% water. It is possible, however, to decrease the $O_2$ to $10^4$ ppm if a hydrogen dopant forming gas is used. Conversely, up to approximately 100 ppm $O_2$ may be present if desired to retard copper sintering.

For temperatures between the 1-3 hour soak at 700°-775° and the peak temperature, it is preferred to change to a dry nitrogen atmosphere with 1-10 ppm $O_2$. Forming gas, if desired, may be mixed with nitrogen to reduce oxygen partial pressure. During the cooling process, it is also possible to increase the $H_2$ level of the atmosphere to help reduce the oxide of the conducting metal, particularly if copper is used.

For air co-firing with silver/palladium or gold, the following firing schedule is preferred. From room temperature to approximately 500°-600° C., heating is 2°-3°/minute; binder burnout occurs prior to approximately 600° C. Unlike the procedure used with copper, there is no need to hold this temperature for an extended period of time in order to obtain less than approximately 250 ppm carbon. Heating continues at a more rapid rate until a temperature of 850°-950° C. is reached.

The invention may be better understood and appreciated by reference to the following examples.

EXAMPLES

EXAMPLE 1

The following substrates were made. Vias and traces were made using a copper-based ink formulation, as set forth in above-referenced application Ser. No. 07/085,077.

anorthite, Q is quartz and 0 is for other, unidentified materials(s).

What is claimed is:

1. A process of making a co-fired ceramic composite package, comprising:
    (a) preparing a slurry comprising (i) a ceramic fraction composed of particles selected from the group consisting of alumina, spinel, cordierite, mullite, forsterite, quartz, and mixtures thereof, and (ii) a glassy fraction composed of 20-57 wt. % alkaline earth oxides, of which calcium oxide comprises 50-100 wt. % and magnesium oxide comprises 0-50 wt. %, 0-10 wt. % aluminum oxide, 23-40 wt. % silicon dioxide, and 25-40 wt. % boron oxide, and (iii) at least one binder;
    (b) casting the slurry to form a tape having a solids portion composed of at least 40 wt. % to 60 wt. % ceramic and the remainder essentially the glassy fraction;
    (c) forming a plurality of via holes at desired positions on the tape;
    (d) applying conductive formulations to selected areas of the tape, including via holes, the formulations including at least one metal selected from the group consisting of copper, silver, palladium, gold, alloys including any of the foregoing, and mixtures thereof to form a conductive green piece;
    (e) heating the conductive green piece to a temperature of less than approximately 800° C. and for a sufficient length of time to ensure substantially complete binder burnout; and
    (f) raising the temperature to a peak temperature of less than approximately 1000° C. for a time sufficient to ensure the piece reaches a density of at least 90% of theoretical density.

2. A process according to claim 1, wherein step (e) is conducted in a non-oxidizing atmosphere.

3. A package made by the process of claim 2.

4. A process according to claim 1 wherein step (f) is conducted in a non-oxidizing atmosphere.

5. A package made by the process of claim 4.

6. A process according to claim 1, further comprising

| Composite | Filler Type | % | Glass Type | % | Firing Temp. | Density | Phases (by relative amts) | Dielectric Constant | Diss. Factor % | Frac. St | Leachability (wt. loss) |
|---|---|---|---|---|---|---|---|---|---|---|---|
| 1. | Cordierite | 60 | D | 40 | 890-930° | 90-95 | C,G,O | 5.3 | <0.3 | 25-30 | <.2 |
| 2. | Quartz Alumina | 45 10 | A | 45 | 875-930° | 90-95 | Q,G,Al,An,O | 5.7 | <0.2 | | |
| 3. | Cordierite | 56 | B,C | 44 | 875-950° | 90-95 | C,G,O | 5.7 | <0.3 | 27-30 | <0.2 |
| 4. | $Al_2O_3$ | 55 | B | 45 | 850-950° | 90-95 | Al,G,An | 7.7 | <0.2 | 35-40 | 0.3 |
| 5. | $Al_2O_3$ Cordierite | 40 15 | C | 45 | 850-950° | 90-95 | Al,G,C,An,O | 7.0-7.3 | <0.2 | 30-35 | <0.2 |
| 6. | $Al_2O_3$ Quartz | 40 20 | B | 40 | 850-950° | 90-95 | Al,G,Q,An | 6.8 | <0.2 | 35-40 | <0.2 |
| 7. | Cordierite Quartz | 31 25 | B | 44 | 875-950° | 90-95 | C,G,Q,O | 5.5-5.7 | <0.3 | 25-30 | <0.2 |

Glass D was a sol-gel composition.

In the above table, glass A was 30.5%, $SiO_2$, 31.5% $B_2O_3$, and 38.0% CaO. Glass B was 33.0% $SiO_2$, 31.0% $B_2O_3$, 6.75% MgO, 20.25% CaO, and 9.0% $Al_2O_3$. Glass C was 33.0% $SiO_2$, 31.0% $B_2O_3$, 11.2% MgO, 15.8 CaO, and 9.0% $Al_2O_3$ Glass D was a sol-gel composition of 35.0% $Si_2O_3$, 32% $B2O3$, 7% MgO, and 26.0% CaO.

The column entitled "Phases" uses the following symbols: C is cordierite, G is glass, Al is alumina, An is prior to step (e) the step of laminating together a plurality of conductive green pieces.

7. A package made by the process of claim 6.

8. A package made by the process of claim 1.

9. The process as defined by claim 1, wherein the ceramic particles are cordierite.

10. The process as defined by claim 1, wherein the ceramic particles are a mixture of quartz and alumina.

11. The process as defined by claim 1, wherein the ceramic particles are a mixture of alumina and cordierite.

12. The process as defined by claim 1, wherein the ceramic particles are a mixture of quartz and cordierite.

13. The process as defined by claim 1, wherein the conductive metal is copper.

14. The process as defined in claim 1, wherein the firing is performed in a nitrogen atmosphere.

15. The process as defined in claim 14, wherein the firing atmosphere also contains hydrogen.

16. The process as defined by claim 1, wherein the firing is performed in air.

17. The process as defined by claim 1, wherein the conductive metal is gold.

18. The process defined by claim 1, wherein the ceramic particles are present in the slurry in an amount of 40–75 wt. %.

19. The process defined by claim 1, wherein the glassy fraction is present in the slurry in an amount of 25–60 wt. %.

20. The process defined by claim 1, wherein the binder is a methacrylate polymer, and wherein the slurry further comprises (iv) a solvent and (v) a plasticizer selected from the group consisting of phthalates and adipates.

* * * * *